US009162013B2

(12) United States Patent
Guggenbichler et al.

(10) Patent No.: US 9,162,013 B2
(45) Date of Patent: Oct. 20, 2015

(54) SUBSTANCE WITH AN ANTIMICROBIAL EFFECT

(75) Inventors: Joseph Peter Guggenbichler, Kössen (AT); Nico Eberhardt, Reutte (AT); Hans-Peter Martinz, Reutte (AT); Heiko Wildner, Füssen (DE)

(73) Assignee: PLANSEE SE, Tyrol (AT)

( * ) Notice: Subject to any disclaimer, the term of this patent is extended or adjusted under 35 U.S.C. 154(b) by 1267 days.

(21) Appl. No.: 12/514,404

(22) PCT Filed: Nov. 13, 2007

(86) PCT No.: PCT/EP2007/009814
§ 371 (c)(1),
(2), (4) Date: Jul. 16, 2009

(87) PCT Pub. No.: WO2008/058707
PCT Pub. Date: May 22, 2008

(65) Prior Publication Data
US 2010/0057199 A1     Mar. 4, 2010

(30) Foreign Application Priority Data
Nov. 13, 2006  (AT) .......................... GM805/2006 U

(51) Int. Cl.
| A01N 59/16 | (2006.01) |
| A01N 25/34 | (2006.01) |
| A61M 25/00 | (2006.01) |
| A61L 27/54 | (2006.01) |
| A01N 59/20 | (2006.01) |
| A61L 29/16 | (2006.01) |
| A61L 31/16 | (2006.01) |
| B29C 45/00 | (2006.01) |
| C01G 39/00 | (2006.01) |
| C01G 39/02 | (2006.01) |
| C01G 41/00 | (2006.01) |
| C09C 1/00  | (2006.01) |
| C09D 5/14  | (2006.01) |

(52) U.S. Cl.
CPC ............. *A61L 27/54* (2013.01); *A01N 59/16* (2013.01); *A01N 59/20* (2013.01); *A61L 29/16* (2013.01); *A61L 31/16* (2013.01); *B29C 45/0013* (2013.01); *C01G 39/00* (2013.01); *C01G 39/02* (2013.01); *C01G 41/00* (2013.01); *C09C 1/0003* (2013.01); *C09D 5/14* (2013.01); *A61L 2300/102* (2013.01); *A61L 2300/104* (2013.01); *A61L 2300/404* (2013.01)

(58) Field of Classification Search
CPC ..... A01N 59/16; C09D 5/16; A61L 2300/404
USPC ....................................................... 424/404
See application file for complete search history.

(56) References Cited

U.S. PATENT DOCUMENTS

| 4,677,016 | A  | * | 6/1987  | Ferziger et al. ............... 428/212 |
| 4,847,163 | A  | * | 7/1989  | Shimamune et al. ......... 428/469 |
| 5,880,067 | A  |   | 3/1999  | Linkous |
| 6,004,667 | A  |   | 12/1999 | Sakurada |
| 6,419,792 | B1 | * | 7/2002  | Nishibori ................... 162/181.4 |
| 7,279,173 | B2 | * | 10/2007 | Schiestel et al. ............. 424/421 |
| 7,445,799 | B1 | * | 11/2008 | Sarangapani et al. ........ 424/618 |
| 2004/0245496 | A1 | * | 12/2004 | Taoda ........................ 252/186.1 |
| 2005/0182152 | A1 | * | 8/2005  | Nonninger et al. ........... 523/122 |
| 2008/0057135 | A1 | * | 3/2008  | Allen et al. .................. 424/618 |

FOREIGN PATENT DOCUMENTS

| EP | 0882398 A      | 12/1998 |
| JP | 8-296031 A     | 11/1996 |
| JP | H08-296031 A   | 11/1996 |
| JP | 9-511156       | 9/1997  |
| JP | 11012479 A   * | 1/1999  |
| JP | 11035414 A     | 2/1999  |
| JP | H11-236699 A   | 8/1999  |
| JP | 20001433369 A  | 5/2000  |
| JP | 2000154320 A * | 6/2000  |
| JP | 2000247805 A   | 9/2000  |
| JP | 3871703 B2     | 1/2007  |
| WO | WO95/18637     | 7/1995  |
| WO | WO 98/14062    | 4/1998  |
| WO | WO 2005103169 A1 * | 11/2005 |
| WO | WO 2008/058707 A3 | 5/2008 |

OTHER PUBLICATIONS

Percival. The effect of Molybdenum on biofilm development. Journal of Industry Microbiology and Biotechnology (1999) vol. 23, pp. 112-117.*
JP,2000-095977 translation.*
S.L. Percival: *The Effect of Molybdenum on Biofilm Development*, J. Industrial Microbiol. Biotechnol., vol. 23, 1999, pp. 112-117.
Database WPI Week 2000067, Thomson Scientific, London, GB; AN 2000-681979, XP002491580, 2000.
Database WPI Week 199916, Thomson Scientific, London, GB; AN 1999-186158. XP002491581, 1999.

(Continued)

Primary Examiner — Cachet Sellman
(74) Attorney, Agent, or Firm — Kilpatrick Townsend & Stockton LLP

(57) ABSTRACT

A method reducing microbial growth uses an inorganic substance consisting of $MoO_2$ and/or $MoO_3$ which causes the formation of hydrogen cations when in contact with an aqueous medium to achieve an antimicrobial effect. The substance is present as a layer or a component of a layer, and is present in combination with one or more materials as a composite material. The composite material has a polymer matrix, and the substance is incorporated at 3 to 50% by weight into the composite material.

34 Claims, No Drawings

(56) References Cited

OTHER PUBLICATIONS

Database WPI Week 200036, Thomson Scientific, London, GB; AN 2000-415748, XP002491582, 2000.
English translation of Korean Examination Report—9-5-2014-025261434 dated Apr. 11, 2014.
English translation of Chinese Examination Report—201310021780.3 dated May 5, 2014.
Examination Report with English translation corresponding to Korean Patent Application No. 10-2014-7018410.
International Search Report mailed Aug. 22, 2008 for International Patent Application No. PCT/EP2007/009814 filed Nov. 13, 2007, 9 pages.
International Preliminary Report on Patentability mailed Feb. 25, 2009 for International Patent Application No. PCT/EP2007/009814 filed Nov. 13, 2007, 11 pages.
Japanese Office Action mailed Jul. 8, 2014 (Reference No. B135506) for Japanese Patent Application No. 2013-080497, all pages.
Japanese Office Action mailed Jul. 8, 2014 (Reference No. B136498) for Japanese Patent Application No. 2013-192024, all pages.

* cited by examiner

SUBSTANCE WITH AN ANTIMICROBIAL EFFECT

FIELD OF THE INVENTION

The invention relates to the use of a substance to achieve an antimicrobial effect.

BACKGROUND OF THE INVENTION

Microorganisms such as bacteria and fungi are omnipresent in our living space and populate the most different types of surfaces. Many microorganisms are pathogens and, consequently, their spreading and/or control play(s) a special part in public health and hygiene. If such microorganisms get into our body, they may be the cause of life-threatening infections. If one contracts such an infection in a hospital, this is called a nosocomial infection.

It is started from the assumption that the Euro amounts in the two-digit billion range for the elimination of damage caused by nosocomial infections are required per year worldwide. Consequently, the control of pathogenic microorganisms plays a special part in public health and hygiene.

Apart from the warding off and/or the killing of undesired microorganisms by means of antibiotics, for instance, prophylactic measures, e.g. the creation of spaces that are hostile to the life of microorganisms are gaining more and more importance. Among these prophylactic measures the use of silver as an additive to organic and inorganic materials over the past few years has quickly gained in importance. Here, silver ions interfere with important functions of microorganisms. Nowadays, it is proceeded from the assumption that silver ions block enzymes and prevent their vital transport functions in the cell. Further effects include the impairment of the structural strength of cells and/or also a damage to the membrane structure. These effects may result in a cell damage and/or cell death. Silver has a very broad active spectrum against multi-resistant germs, as well. Small doses are sufficient for achieving a long-term effect. This is called an oligodynamic effect. Organic compounds are still added in some cases in order to increase the effectiveness of silver. It is always of importance that sufficient silver ions are present. Consequently, a nanoscale silver powder, so-called nanosilver, is used in order to achieve a large particle surface.

Silver does not have any toxic side effects in a broad dosage spectrum. Only highly increased accumulations of silver in the body may result in an argyria, an irreversible, slate-gray discoloration of skin and mucous membranes. In addition, increased silver concentrations may cause taste disorders, disorders of the sensitivity to smell and cerebral convulsions.

Moreover, it must be mentioned that, in general, the interaction between nanoscale particles and the human organism has not been sufficiently investigated as yet. Broad investigation programs have only been started recently. The antimicrobial effectiveness of silver is not sufficient for many applications. The effectiveness is only given up to 0.25 of molar saline solution. Beyond that, the formation of silver chloride takes place. The essential disadvantage of the use of nanosilver resides in a non-satisfactory cost situation. On the one hand, this is due to the high price of silver and, on the other hand, the processing of silver to nanoparticles is time-consuming and expensive. A further problem arises in the processing of nanosilver due to the formation of agglomerates, aggregates and clusters. Due to this, the active surface is reduced and, as a further consequence, the antimicrobial effect. In order to prevent this, nanosilver is deposited on particle surfaces of a carrier, e.g. $TiO_2$, which, in turn, increases the production costs.

Consequently, there has been no lack of attempts at detecting an antimicrobial, oligodynamic and disinfecting effect in other metals. Copper, for instance, also has a strong antimicrobial effect, but at a too high zytotoxicity. The result of a search in the Internet encyclopedia Wikipedia under the search word oligodynamics is that, so far, this effect has been found in the following metals, in a descending order in accordance with their effectiveness: mercury, silver, copper, tin, iron, lead and bismuth. Gold and osmium, two noble and expensive metals, have this effect, as well.

However, it is required for many applications that, in addition to a sufficient antimicrobial effectiveness, the active substance does not have any zytotoxicity and thrombogeneity and is in general biocompatible. Active substances such as mercury, bismuth or copper do not have these properties due to their high zytotoxicity and the non-given biocompatibility.

A plurality of patent and non-patent literature deals with the production and the use of nanosilver. Further metals and inorganic compounds are only described in isolated cases. U.S. Pat. No. 5,520,664 discloses a catheter made of plastic. Atoms are introduced by means of ion implantation to achieve an antimicrobial effect. Silver, chromium, aluminum, nickel, tungsten, molybdenum, platinum, iridium, gold, silver, mercury, copper, zinc and cadmium are mentioned as a metal with an antimicrobial effect. However, only silver and copper are mentioned in the examples and special embodiments.

JP 2001-54320 describes a plastic material which contains 0.005 to 1% by weight of a mixture of molybdenum trioxide and silver oxide. The invention relates to a film consisting of an antibacterial resin component and of components which may be used for the material of partitions of clean rooms, for the uppermost layer of floor coverings, linings, briefcases, desk pads, tablecloths, packaging bags, textiles and the like. Here the problem is that in the case of the incorporation of an inorganic, antibacterial active substance the transparency of the plastic material, e.g. of vinyl chloride resin, is lost. The loss of transparency is avoided by the admixture of oxide of the hexavalent molybdenum. This application readily reveals that, upon the exceeding of the weight ratio of molybdenum trioxide to silver oxide of 95:5, an antibacterial effect can no longer be achieved. Consequently, no antibacterial effect is attributed to molybdenum oxide per se. If the ratio of molybdenum oxide to silver oxide is less than 30:70, i.e. with small shares of molybdenum oxide, a discoloration of the vinyl chloride resin takes place.

An antimicrobial plastic material is described in JP 2001-04022, which contains both organic components with an antimicrobial effect and metallic components. Silver, platinum, copper, zinc, nickel, cobalt, molybdenum and chromium are mentioned as a metallic component with an antimicrobial effect. However, silver and copper are again only mentioned as being active in the examples and preferred embodiments.

A glaze for ceramic components is disclosed in JP 2000-143369, which contains silver molybdate. Here, 0.01 to 1% of silver molybdate are added and converted to metallic silver. The effect is increased by the addition of 10 to 50% of titanium oxide.

An antimicrobial effect can also be achieved by means of components with a photooxidative effect. Due to this, reactive free radicals are formed, which damage the microorganisms. JP 11012479 describes an antimicrobial plastic material which contains an organic and an inorganic component. Metallic particles such as silver, zinc and copper and further compounds such as calcium zinc phosphate, ceramics, glass powder, aluminum silicate, titanium zeolite, apatite and calcium carbonate are mentioned as an example of inorganic components. Here, metal oxides such as zinc oxide, titanium oxide or molybdenum oxide act as a catalyst for the photooxidative effect. Consequently, JP 11012479 reveals that the antimicrobial effectiveness is only achieved, if the photooxidative mechanism occurs, i.e. the prerequisite for the effectiveness is the action of electromagnetic radiation.

SUMMARY OF THE INVENTION

The availability of inexpensive materials with an antimicrobial effectiveness is gaining more and more in importance. These properties are in particular important, if many people are crowded together or in cases where great demands are made on hygiene such as this is e.g. the case in hospitals, medical practices, nursing homes and public institutions. Here, the reduction of the nosocomial infection is of special importance. It is estimated that infections may develop in 0.5% of all hip joint implants and in 2 to 4% of all knee joint implants. There is in particular a high risk of infection in catheters. In addition to this, there is also a demand in many further fields of application to control and/or prevent the populating and propagation of microorganisms.

In addition to the availability of a substance with an antimicrobial effect, it is also of further interest that the effectiveness of the antimicrobially active substance is not attenuated if it is incorporated in composite materials from which the corresponding articles such as catheter implants, filters, tubes, containers, cables, etc. are then produced.

As a rule, the production of plastic materials is inexpensive and their handling is simple. Thus, they are especially preferred in many applications. However, here, there is the problem that different types of plastic material must be used for the different applications, since the properties such as flexibility and/or rigidity and working stress depend on the type of the plastic material. Every plastic material is e.g. not suitable for every application, e.g. catheters or infusion bags must still have a certain flexibility as opposed to implants or waste containers, for instance. Consequently, it must be tested for each type of plastic material used whether the antimicrobial substances retain their effectiveness in connection with the corresponding plastic material and/or how they must be accordingly used with the plastic material in order to obtain their effectiveness. However, this results in time-consuming and expensive and extensive test series, namely anew for each desired application, which, in turn, results in higher production costs.

Consequently, it is the object of the present invention to provide an active substances which has a high antimicrobial effectiveness comparable to that of nanosilver. The active substance is to be only slightly zytotoxic and thrombogenic and also is to have a high general biocompatibility for medical applications. Moreover, the active substance is to have a high cost-benefit ratio and favorable processing properties. Moreover, it is advantageous if the substance does not only have an antimicrobial effect in the form of nanoscale particles (particle size of less than 100 nm), but also in the form of non-respirable particles (particle size of more than 500 nm) and/or also in a compact form. Moreover, it is desirable that a composite material is made available which contains the antimicrobially active substance and which has many uses, the substance retaining its full effect in the composite material.

DESCRIPTION OF THE SPECIFIC EMBODIMENTS

This complex object is attained by using an inorganic substance which causes the formation of hydrogen cations when being contacted with an aqueous medium in order to obtain an antimicrobial effect, characterized in that the substance contains molybdenum and/or tungsten.

Whereas the oligodynamic effect, i.e. the damaging effect of metal cations on living cells, is used in the inorganic active substances available to date, the formation of hydrogen cations causing a lowering of the pH value in the medium being in contact with the substance is utilized in the present invention. Here, free protons immediately attach themselves to a water molecule forming oxonium ions ($H_3O^+$) due to their very small radius. If the concentration ratios permit it a linkage of the oxonium ions to several water molecules can take place. Consequently, in addition to $H^+$, the cations formed by the reaction of $H^+$ with water and their hydrates are also designated as hydrogen cations. In addition to the oxonium ion ($H_3O^+$) these are the Zundel cation ($H_5O_2^+$) and the Eigen cation ($H_9O_4^+$).

Molybdenum oxide reacts e.g. with water to form molybdic acid ($H_2MoO_4$), which again reacts with $H_2O$ to form $H_3O^+$ and $MoO_4^-$ or $MoO_4^{2-}$. Tungsten oxide also forms tungstic acid ($H_2WO_4$) with $H_2O$, which reacts with $H_2O$ to form $H_3O^+$ and $WO_4^-$ or $WO_4^{2-}$. In accordance with Arrhenius the hydrogen cation is the carrier of the acidic properties. The pH value is the negative decimal logarithm of the numerical value of the concentration of hydrogen ions in mole/liter. For a pure neutral solution of water the hydrogen ions and the $OH^-$ (hydroxide) ions have the same value ($10^{-7}$ mole/l) and the pH value is 7. If a substance now forms hydrogen cations when it is in contact with an aqueous medium, an increase in the hydrogen cation value takes place and, thus, the aqueous medium becomes acidic.

Now, it surprisingly turned out that substances forming hydrogen cations when in contact with an aqueous medium have an excellent antimicrobial effectiveness. An essential advantage also resides in the fact that the substances are practically not consumed. This is in particular the case if the substance has a low solubility in the aqueous medium. The solubility is preferably less than 0.1 mole/liter. The solubility of molybdenum oxide and tungsten oxide is less than 0.02 mole/liter. Consequently, the antimicrobial effect is almost unrestrictedly present in terms of time.

The aqueous medium may e.g. be water, a solution or a suspension. Examples of a solution are the body fluid and of a suspension liquid tissue. Here, it is sufficient that the aqueous medium is present on the substance surface in the form of a thin film. The inventive effect is already achieved at a thickness of the film in the nanometer range as this is the case with adsorbate. Consequently, the inventive effect already occurs if the substance is exposed to air. Due to the formation of hydrogen cations, a lowering of the pH value typically to <6, preferably <5, takes place. The acidic environment generated by this causes a killing of the microorganisms.

The effect of substances according to the invention was investigated in broadly designed test series. Here, the antimicrobial effect and, partly, also the zytotoxicity and thrombogeneity, were examined. As set forth in the examples molybdenum- and tungsten-containing materials the surface of which is oxidized or which are present in oxidized form are especially effective. Molybdenum may be present in different oxidation states (VI, V, IV), it participates in redox processes forming relatively weak complexes with physiologically important compounds. Although molybdenum has an essential biochemical part, it does not bind to physiologically important compounds to a sufficiently strong degree in order to have a serious blockage effect on metabolic processes. Therefore, a toxicity for the human organism is also not given. It must be proceeded from the assumption that molybdenum is taken in by and transported in animals and plants in the form of a simple molybdate ion $[MoO_4]^{2-}$. These $[MoO_4]^{2-}$ anions can penetrate the cell membranes without damaging the cell. Consequently, it must be proceeded from the assumption that molybdenum is not zytotoxic. Moreover, a thrombogenic effect is also not known. Therefore, molybdenum is also suited for medical applications. Tungsten-containing materials also show a high antimicrobial effectiveness. At present, no unequivocal statement can be made as yet on the thrombogeneity since first tests suggest a certain thrombogenic effect. It must still be clarified whether this is an intrinsic property of tungsten or depends on the processing state.

Apart from molybdenum- and tungsten-containing materials an antimicrobial effect connected with a lowering of the pH value was also found in niobium oxide, manganese oxide and silicon carbide.

A method was used for the characterization of the antimicrobial effectiveness, which is described in detail in the following specialized essays:

Fremdkörper-assoziierte Infektionen in der Intensivmedizin—Therapie und Prävention, J. P. Guggenbichler, Antibiotika Monitor 20 (3), 2004, pages 52-64

Inzidenz und Prävention Fremdkörper-assoziierter Infektionen, J. P. Guggenbichler, Biomaterialien 5 (4) 2004, pages 228-236.

In particular, the method of the roll-out culture which is described there proved its worth for examining the antimicrobial effect. Here, a sample of the active substance is put into a germ suspension for a specific period of time, for instance 3 hours. Germs grow on the surface. After this period of time the samples are rolled across a so-called agar plate and put into a sterile physiological saline solution. This procedure is repeated several times every three hours. This repeated roll-out activity at an interval of three hours gives information about the fact whether and with which degree of efficiency a germ-reducing or germ-killing effect occurs. This method can be used for the examination of different microbes, bacteria and viruses. The examinations regarding the proof of the effect of the substances according to the invention were separately implemented for the reference strains *Pseudomonas aeruginosa, Escherichia coli* and *Staphylococcus aureus*. Silver and copper were used as reference materials.

As already mentioned, it was possible to achieve the best results with substances containing molybdenum and tungsten. Here, it is essential for the invention that molybdenum oxide or tungsten oxide is formed in the boundary area between the molybdenum- or tungsten-based active substance. If this oxide formation does not take place to a sufficient degree or with a corresponding morphology, then no antimicrobial effect is present. This also explains why molybdenum and tungsten have not been used as antimicrobially active materials to date.

An antimicrobial effectiveness can be adjusted by means of a thermal pre-oxidation at temperatures of advantageously more than 300° C. The pre-oxidation may also be carried out chemically or electrochemically. This pre-oxidation is necessary in the case of solid Mo and W samples. Here, it became apparent that, as compared with an oxide film formed in situ, a material pre-oxidized by means of an annealing has a better antimicrobial effect. A pre-oxidation must in particular be carried out, if the conditions of use do not trigger any sufficient oxidation. Here, it is also decisive that the oxide film has a large specific surface.

In addition to pure molybdenum and pure tungsten, the compounds and alloys of these compounds which are sufficiently stable and form an oxide film on their surface are also effective. The molybdenum compounds having an antimicrobial effectiveness include molybdenum carbide, molybdenum nitride, molybdenum silicide and molybdenum sulfide. Molybdenum, molybdenum oxide and the aforementioned substances are also commercially available in a very fine form with particle sizes according to Fisher of <1 μm. Among the suitable molybdenum alloys Mo with from 0.1 to 1% by weight of $La_2O_3$, Mo with 0.5% by weight of Ti, 0.08% by weight of Zr, from 0.01 to 0.04% by weight of C, Mo with from 5 to 50% by weight of Re and Mo with 1.2% by weight of Hf, from 0.02 to 0.15% by weight of C must be mentioned.

These alloys form an antimicrobially active oxide film on the surface. In the case of tungsten, tungsten materials are also effective which form an oxide film in situ or by means of a preceding annealing. In addition to oxidized pure tungsten, the oxides of tungsten are effective. Here, tungsten blue oxide ($WO_{2.84}$) and $WO_3$ are especially mentioned. The tungsten alloys W with from 0.1 to 1% by weight of $La_2O_3$ and W with from 1 to 26% by weight of Re also have a good antimicrobial effectiveness. Tungsten carbide, tungsten silicide and tungsten sulfide are especially suitable among the possible tungsten compounds forming an oxide film on the surface.

Whereas the antimicrobial effect only occurs to a sufficient degree in silver, if silver is present in a very fine-grained state, the substances according to the invention also have an antimicrobial effectiveness if they are present in a compact dense form. The tests have shown that the effectiveness is still increased if the surface is enlarged. Therefore, it may be advantageous for many applications if the substance is present in a porous form.

The effectiveness is also given if the substance is present as a layer or a component of a layer. Layers of molybdenum oxide and layers of tungsten oxide layers and/or also layers of molybdenum and layers of tungsten, which are oxidized in situ or oxidized by means of a pre-oxidation if no sufficient oxidation takes place in situ, proved to be especially advantageous. The layers may be deposited on plastic materials, ceramics or metals. Especially suitable deposition processes are thermal evaporation, sputtering, chemical vapor deposition, electroprecipitation and electric arc evaporation. Molybdenum oxide layers can e.g. be produced by means of chemical vapor deposition by the decomposition of molybdenum hexacarbonyl ($Mo(CO)_6$) at atmospheric pressure. A organometallic CVD (MOCVD) is also possible. Here, molybdenum acetyl acetonate ($MoO_2(CH_3COCH_2COCH_2)_2$) can e.g. be used as organometallic compound. Molybdenum oxide films can be produced with these organometallic compounds at temperatures ranging from approx. 400 to 500° C., $Mo_9O_{26}$ and $Mo_4O_{11}$ being also detectable apart from $MoO_3$. The grain size of <1 μm with layer thicknesses in the range of a few μm furthers the antimicrobial effectiveness. Molybdenum oxide and tungsten oxide films can also be deposited by means of the reactive electron-beam evaporation. These films also have a very fine-grained structure with pores of a size ranging from 50 to 100 nm.

Electrophoresis and sol-gel processes must still be mentioned as especially suitable deposition methods.

If the layers are deposited on metals, the common implant materials such as titanium, iron and cobalt and their alloys are to be preferred. In the case of ceramic substrate materials, as well, it is preferred to proceed from established materials such as $ZrO_2$ and $Al_2O_3$, whose purity is better than 99% by weight. The layers may also be deposited on glass or glass ceramics.

As already mentioned, the effectiveness increases if the substance has a surface that is as large as possible towards the aqueous medium. Especially good results can be achieved if the layer has a spongy porous structure with a pore size of from 50 to 900 μm. Such porous structures can e.g. be produced by depositing the antimicrobially active substance in the form of a slurry or from the gaseous phase with an optional subsequent annealing. A large surface can also be achieved, if the layer is present in the form of island-like, substantially unlinked agglomerates. It is especially advantageous if these island-like agglomerates cover 40 to 90% of the surface of the substrate material. The preferred size of the individual substance agglomerates is less than 5 μm. It may be sufficient for many applications, if the substance according to the invention is used in powder form. Accordingly, it is advantageous if a very fine-grained powder is used, i.e. that the particle size according to Fisher is <5 μm, preferably less than 1 μm.

The best results could be achieved with metallic composite materials and/or composite powders. Here, the composite material may also be present in the form of a composite powder. These metallic composite materials contain, in addition to the substance according to the invention, a further chemically nobler metal. Here, the interaction between the chemically nobler metal furthers the formation of hydrogen cations. Mixtures of the substances according to the invention with a nobler metal even have an antimicrobial effect, if the samples are not pre-oxidized.

Here, the chemically nobler metal is preferably silver, copper, tin and their alloys. The metallic composite materials Mo—Ag, Mo—Cu, Mo—Sn, W—Ag, W—Cu and W—Sn are especially advantageous. Here, the content of Mo and/or W is preferably 10 to 90 atom %, it having been possible to achieve the best results with 30 to 80 atom %.

The use of silver is advantageous, if the material must not be zytotoxic and thrombogenic. However, these properties do not play any part in many applications. Here, fittings for hygiene rooms are mentioned by way of example. Here, copper may be used instead of the expensive silver, which surpasses silver in its antimicrobial effectiveness. A very high effectiveness is also given if an Mo—Cu or W—Cu powder is added to other materials. In addition, the metallic composite material may also be present in a compact form, as a layer or e.g. as a porous shaped body. The production may advantageously be carried out by means of infiltration techniques for compact composite materials.

Moreover, the substance according to the invention can be used for the production of an antimicrobial plastic material.

Here, a composite material containing the substance according to the invention is especially of interest, if this composite material contains one or more material(s), at least one material thereof containing a polymer matrix being formed from a cross-linkable polymer mixture. This polymer mixture preferably contains an unsaturated polyolefin (A) which contains a total amount of carbon-carbon double bonds/1000 carbon atoms of more than 0.37.

It turned out that this composite material can be used on a multi-purpose basis.

The use of the unsaturated polyolefin in the polymer mixture results in the fact that the polymer mixture becomes cross-linkable. This preferably takes place by the double bonds present in the polymer mixture. Then, the degree of the cross-linking can be controlled via these double bonds on the basis of the number of carbon-carbon double bonds in the polyolefin, but also in the polymer mixture. The degree of cross-linking, however, determines the flexibility and/or rigidity of the polymer. Polymers with a high degree of cross-linking also have a higher rigidity than polymers with a lower degree of cross-linking. Consequently, the composite material according to the invention can be used in the most different applications.

Moreover, it is preferred if the cross-linkable polymer mixture contains a further copolymer (B).

Here, the term "total amount of carbon-carbon double bonds" in connection with the term "unsaturated polyolefin (A)" relates to double bonds originating from vinyl, vinylidene and/or trans-vinylene groups. The amount of any type of double bonds is determined in accordance with a process as it is described in the experimental part of EP 1 731 566.

The cross-linking properties of the polymer mixture can be controlled by the introduction of the double bond so that the desired degree of cross-linking can be adjusted.

A total content of carbon-carbon double bonds of at least 0.40 per 1000 carbon atoms is preferred for the different applications. A content of 0.45 to 0.80 per 1000 carbon atoms is of special interest.

Moreover, it is preferred that the total content of vinyl groups in the unsaturated polyolefin is higher than 0.11 per 1000 carbon atoms. Here, the especially preferred range is from 0.15 to 0.80 per 1000 carbon atoms, however, it may also be higher.

It is known that two types of vinyl groups are found in polymers. The one type is produced in a polymerization process by means of a β-cleavage reaction of secondary radicals or is the result of a so-called chain transfer agent. The second type which is preferred in the present invention is produced by means of the polymerization between at least one olefin monomer and at least one polyunsaturated monomer.

Both types of vinyl groups may be contained in the polymer mixture of the present invention. However, it is preferred that the content of vinyl groups which are formed by the polymerization between at least one olefin monomer and at least one polyunsaturated monomer is at least 0.03/1000 carbon atoms. A content of from 0.06 to 0.40/1000 carbon atoms is preferred.

The unsaturated polyolefin may be both unimodal and multimodal, e.g. bimodal, in the present invention and have a density of from 0.860 to 0.960 g/cm$^3$, preferably of from 0.880 and 0.955 g/cm$^3$, especially preferred of from 0.900 to 0.950 g/cm$^3$.

Moreover, it is preferred that the unsaturated polyolefin is produced from an olefin monomer, ethylene and propylene being preferred, and at least one polyunsaturated monomer by means of polymerization.

Here, the polymerization can be carried out in accordance with any optional known method, however, a radicalic polymerization at a high pressure as it is described in greater detail in WO93/08222 is to be preferably used.

Moreover, it is preferred that the unsaturated polyolefin contains at least 60% by weight of ethylene monomer. A content of at least 70% by weight is more preferred, a content of at least 80% by weight is especially preferred and one of at least 90% by weight is most preferred.

The polyunsaturated comonomers are preferably dienes. Dienes selected from a group consisting of:

a monomer having a carbon chain being free from heteroatoms and containing at least eight carbon atoms, at least four carbon atoms being between the non-conjugated double bonds and at least one of these double bonds being in a terminal position, a siloxane in accordance with the formula I,

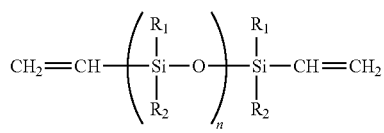

wherein R1 and R2 may be different or similar alkyl groups consisting of 1-4 carbon atoms and an alkoxy group which, again, has 1-4 carbon atoms and n=1-200, and an α,ω-divinyl ether in accordance with the formula II $$H_2C=CH-O-R-CH=CH_2$$

wherein R is a —$(CH_2)_m$—O—, or a —$(CH_2CH_2O)_n$— or —$CH_2$—$C_6H_{10}$—$CH_2$—O— and m=2 to 10 t and n=1 to 5,
are especially preferred.

The dienes may be used in all conceivable combinations.

The dienes used in the present invention and their production are described in greater detail in WO 93/08222, WO96/35732 and in WO 97/45465, reference being made thereto.

It is especially preferred that the dienes are selected from a group consisting of: 1,7 octadiene; 1,9-decadiene; 1,11-dodecadiene; 1,13-tetradecadiene; tetra-methyl divinyl disiloxane; divinylpoly(dimethyl siloxane); and 1,4-butadiene divinylether or a combination thereof.

In addition to the polyunsaturated monomers, further comonomers may be used in the polymerization such as e.g. $C_3$-$C_{20}$ alpha-olefins, e.g. propylene, 1-butene, 1-hexenes and 1-nonene, or polar comonomers such as e.g. alkyl acrylates, alkyl methaacrylates and vinylacetates.

However, the content of polar monomers in the unsaturated polyolefin (A) is less than 150 micromoles, preferably less than 125 micromoles, especially preferred less than 100 micromoles.

Moreover, it is preferred that the polymer mixture contains a further copolymer (B). This copolymer (B) is preferably polar.

In addition, the polar copolymer (B) like the unsaturated polyolefin may contain the compounds described above and, thus, the corresponding number of carbon-carbon double bonds. The cross-linkability of the polymer mixture is still increased by this.

Here, the content of carbon-carbon double bonds in the polar copolymer is at least 0.15 per 1000 carbon atoms. A content of 0.20 to 0.35 per 1000 carbon atoms is preferred.

However, the polar copolymer distinguishes itself in that it contains polar monomer units, namely in an amount of at least 500 micromoles per gram of polar copolymer, preferably of 700 micromoles, especially preferred of 900 micromoles and most preferred 1100 micromoles per gram of polar copolymer.

The polar copolymer is produced from an olefin, preferably ethylene, and a polar comonomer by means of a polymerization. Here, at least one or a mixture of the polyunsaturated monomer(s) described above may be present.

Preferably, the polar comonomer is $C_3$ to $C_{20}$ monomers, which contain e.g. hydroxyl, alkoxy groups, carbonyl, Carboxy, ester groups or a mixture thereof.

It is also preferred that the monomer units are selected from a group consisting of alkyl acrylates, alkyl methaacrylates and vinylacetates.

It is especially preferred that the comonomer is comonomers selected from the group consisting of $C_1$ to $C_6$ alkyl acrylates, $C_1$ to $C_6$ alkyl methacrylates, or vinyl acetates.

Polar monomers from the group consisting of alkyl esters of methacrylic acid such as e.g. methyl, ethyl or butyl methacrylate or vinyl acetate are considered to be especially preferred. Due to its thermal stability the acrylate type is preferred.

The polar copolymer (B) should preferably have a so-called melt flow rate of $MFR_{2.16/190° C.}$ 0.5 to 70 g/10 min., more preferred of 1 to 55 g/10 min., most preferred of 1.5 to 40 g/10 min.

The cross-linkable polymer mixture is preferably produced by mixing the two components—unsaturated polyolefin (A) and polar copolymer (B). An exact description of the production process of the individual components (A) and (B) is found in EP 1,731,566.

Preferably, the cross-linkable polymer mixture contains of from 5 to 60% by weight, more preferred of from 8 to 50% by weight, especially preferred of from 10 to 40% by weight, and most preferred of from 15 to 35% by weight, of the polar copolymer based on the total weight of the cross-linkable polymer mixture.

Moreover, it is preferred that the cross-linkable polymer mixture has a total content of carbon-carbon double bonds per 1000 carbon atoms of more than 0.30. A total content of more than 0.35; 0.40; 0.45, 0.50; 0.55, in particular of more than 0.60, of carbon-carbon double bonds per 1000 carbon atoms is especially preferred. Here, the determination is based on the content of vinyl, vinylidene and trans-vinylidene groups per 1000 carbon atoms both of the unsaturated polyolefin (A) and the polar copolymer (B).

Here, the content of vinyl groups is preferably of from 0.05 to 0.45 vinyl groups per 1000 carbon atoms, more preferred of from 0.10 to 0.40, especially preferred of from 0.15 to 0.35 per 1000 carbon atoms.

The polymer matrix in the present invention is formed by the cross-linking of the described cross-linkable polymer mixture.

This is preferably done by means of a cross-linking agent. This agent regenerates radicals and, thus, starts the cross-linking reaction. Compounds containing at least one —O—O— or one —N=N— bond are especially preferred agents. The use of peroxides is especially preferred.

Di-tert.-amyl peroxide; 2,5-di(tert.-butyl peroxy)-2,5-dimethyl-3-hexane; 2,5-di(tert.-butyl peroxy)-2,5-dimethyl hexane, tert.-butylcumyl peroxide; di(tert.-butyl)peroxide; dicumyl peroxide; di(tert.-butyl peroxide-iso-propyl)benzene, butyl-4,4-bis(tert.-butyl peroxy)valerate; 1,1-bis(tert.-butyl peroxy)-3,3,5-trimethyl cyclohexane; tert.-butylperoxy benzoate, diene benzoyl peroxide are e.g. suitable as a peroxide.

The antimicrobially active substance is preferably admixed prior to the cross-linking reaction and, together with the polymer matrix, forms the composite material.

Here, it is preferred that the substance according to the invention is incorporated into plastic material, in particular the polymer matrix described above with from 0.1 to 50% by volume. These are 3 to 15% by volume in an especially advantageous embodiment.

The cross-linking reaction takes place at the conditions customary for it, i.e. e.g. at a temperature of at least 160° C.

It is preferred that the cross-linked polymer matrix has an elongation at break, a so-called hot-set elongation, of less than 175%, more preferred a value of less than 100%, especially preferred of less than 90%, determined in accordance with the IEC 60811-2-1 method. The value of the elongation at break correlates with the degree of the cross-linking. The lower the value of the elongation at break, the higher the degree of cross-linking of the polymer mixture.

The degree of cross-linking and, thus, the rigidity of the polymer mixture can be regulated by means of the content of double bonds and the amount of the radical initiator, as already mentioned.

A highly cross-linked polyethylene is preferred in many applications.

The composite material according to the invention can be easily processed by means of injection molding. A granulate compounded in an extruder is preferably used for the production of the injection-molded composite material, which, at the same time, is subjected to the cross-linking reaction. As opposed to the production of polymer matrix composite materials that are produced with silver nanopowder, a carrier for the active substance can be renounced in order to avoid the formation of agglomerates or clusters, if the substances according to the invention are used.

In addition to the degree of cross-linking which is individually adjustable and, thus, the possibility of different applications as they will e.g. still be described in the following, the used polymer matrix in the composite material also has a good mechanical and thermal stability.

As an additive to the plastic material and/or polymer matrix molybdenum oxide, pre-oxidized molybdenum, tungsten oxide, pre-oxidized tungsten, Mo—Cu, W—Cu, Mo—Ag and W—Ag impart an excellent antimicrobial effectiveness to the plastic material and/or the polymer matrix composite material. It was possible to achieve the best results with Mo—Cu, W—Cu, Mo—Ag and W—Ag. Here, as well, it must again be proceeded from the assumption that the chemically nobler metal furthers the oxidation of the non-nobler one and, thus, as a result, the production of hydrogen ions. If an Mo—Cu, W—Cu, Mo—Ag or W—Ag composite powder is used as the additive, it is again of importance that the molybdenum and/or tungsten phase(s) and the copper and/or silver phase(s) are present in a very fine form. A composite powder produced by means of a coating process can e.g. be used. The particle size of the composite powder is preferably <5 µm.

The substance according to the invention may also be present in combination with one or several ceramic materials. The production takes e.g. place by means of hot pressing. Alumina, titanium oxide, silicon oxide, silicon carbide and zirconium oxide are in particular suitable as the ceramic phase. In order to be able to use the customary production methods and conditions for ceramics, additives according to the invention, which are present in the highest oxidation state, such as e.g. $MoO_3$ and $WO_3$, are suitable. In addition thereto, metallic Mo and W may still be present.

Thus, the following combinations of materials result as suitable ceramic composite materials: $Al_2O_3$—$MoO_3$, $Al_2O_3$—$WO_3$, $ZrO_2$—$MoO_3$, $ZrO_2$—$WO_3$, $Al_2O_3$—Mo—$MoO_3$, $Al_2O_3$—W—$WO_3$, $ZrO_2$—Mo—$MoO_3$, $ZrO_2$—W—$WO_3$, $TiO_2$—$MoO_3$, $TiO_2$—$WO_3$, $TiO_2$—Mo—$MoO_3$, $TiO_2$—W—$WO_3$, $SiO_2$—$MoO_3$, $SiO_2$—$WO_3$, $SiO_2$—Mo—$MoO_3$ and $SiO_2$—W—$WO_3$. Here, the advantageous share of $MoO_3$ or $WO_3$ is from 0.001 to 50 mole per cent. The advantageous mole ratio of $ZrO_2$, $Al_2O_3$, $TiO_2$ or $SiO_2$ to $MoO_3$ or $WO_3$ is from 1 to 100.

A plurality of advantageous applications result for the substances according to the invention due to the high antimicrobial effectiveness. These include implants and other instruments for medical technology. As regards implants, the substances according to the invention can, however, be especially advantageously used in catheters, stents, bone implants, tooth implants, vascular prostheses and endoprotheses.

The advantageous applications in the field of catheters include the port catheters and bladder catheters. Port catheters customarily comprise a chamber with a silicone membrane and a connected tube. To date, the chamber customarily consists of a plastic material, plastic-sheathed titanium or ceramics. Now, the catheter or chamber of the catheter may be produced from the substance according to the invention or from a material containing the substance. However, it is also possible to provide the catheter or parts of the catheter with a layer according to the invention. Very good results can be achieved if the chamber consists of an Mo—Ag, the Ag content being of from 1 to 40% by weight. According to the prior art this chamber is again sheathed with a plastic material. Moreover, it is also advantageous if the plastic material and/or the silicone membrane contain(s) the substance.

Problems due to bacteria contamination may also occur in Luer lock connections, three-way cocks and cock benches, and, thus, they represent preferred applications for the substance according to the invention.

It is advantageous in coronary stents to apply the substance according to the invention by means of a coating process onto a stent made of a shape memory alloy, e.g. nitinol. The substance according to the invention may also be advantageously used in ureter stents. Ureter stents are customarily produced from polyurethane or silicone. Here, the substance according to the invention may be added to the polymer material or, again, be applied onto the surface as a layer.

Bone implants are in contact with the tissue fluid. Here, as well, the substance according to the invention can develop its effect. Here, it is advantageous to apply the substance according to the invention as a layer. An example of a bone implant is the hip joint. It is advantageous to make the layer smooth in the area of the condyle, whereas the implant shaft may be provided with a spongy coating. Since the substance according to the invention, as already mentioned, can be easily incorporated into a polymer material, it is also suitable for achieving an antimicrobial effect in vascular protheses or the hernia omentum. The medico-technical uses also includes the use as a surgical case.

Moreover, the substance according to the invention can be used in any type of containers as they are used in medicine. The use of the substance according to the invention in nose spray bottles is advantageous, since there is a high risk of the contamination with microorganisms.

Apart from the purely medical and veterinary medical usability, a plurality of application in the field of hygiene is possible. The substance is suitable as an additive for absorbent sanitary articles or wound coverings. Sanitary articles and wound coverings contain polymer fibers or lattices. Now, the substance according to the invention can be advantageously deposited on the surface of the fibers and/or lattices or the fibers and/or lattices may contain the substance.

Moreover, it became apparent that the substance according to the invention may be used as an additive in wound coating sprays—also called "liquid wound coating plaster"—, as they are available in the trade nowadays, in order to intensify the antimicrobial effect of the same or to maintain it for a longer period of time, since, frequently, they only have a short-term antimicrobial effect. Here, the use of the substance according to the invention is preferred, if it contains molybdenum or consists thereof. It is more preferred if molybdenum and/or its compounds and alloys is/are used in the wound coating sprays in a concentration of from 0.05 to 1.0% by volume, especially preferred of from 0.1 to 0.5% by volume.

The substance according to the invention is also suitable as an additive for varnishes, coating substances and adhesives. Here, it proves its worth if the varnish, coating substance or adhesive contains of from 0.01 to 70% by volume of the substance. The especially preferred range is from 0.1 to 40% by volume. $MoO_3$ and/or $WO_3$ are especially suitable as additives for cost-sensitive products. Here, the preferred particle size according to Fisher is 0.5 to 10 μm. Here, the addition of noble metals such as e.g. silver can be renounced. However, if an especially high effectiveness is required, additives on the basis of W—Ag, W—Cu, Mo—Ag, Mo—Cu, Mo—Sn und W—Sn are to be preferred. Particles, again preferably with a size according to Fisher of from 0.5 to 10 μm, may be incorporated in liquid varnish systems such as two-component polyurethane varnishes by means of conventional dispersing techniques.

Apart from applications in the fields of medicine and hygiene the substance according to the invention may also be used as an additive for a personal hygiene product. Ointments, soaps, dental cleanser compositions, toothpastes, adhesives for dentures, toothbrushes, intertooth cleansing agents and tooth cleansing chewing gums are mentioned here as advantageous products.

Moreover, the substance according to the invention may also advantageously used as an additive for a filter. Here, metallic composite materials proved their worth to a special degree, which, in addition to tungsten or molybdenum, still contain a nobler phase such as e.g. silver, copper or tin. Here, the filter may again consist of polymer fibers containing the substance or being coated with the substance.

At present, antibacterially active substances are already used as additives for items of clothing and shoe insoles. In this field of application, as well, the lower costs as compared with nanosilver can be advantageously used. Here, the polymer fiber may contain the substance or the substance may be present on the polymer fiber in a deposited form.

Since the substance according to the invention can be easily admixed to varnishes, coating substances and/or plastic materials, products produced therefrom are suitable as furnishings, in particular for hygiene rooms.

Apart from these fields of application, many further fields of application present themselves for the substance according to the invention, in particular for products which are frequently in contact with living beings. These include e.g. switches, fittings, credit cards, keyboards, cell phone housings, coins, bills, door handles and parts of the inside furnishings of a public means of transport. A further advantageous use is components for air-conditioning systems. The substance according to the invention is e.g. suitable for air-conditioners in means of transport, e.g. automobiles. The radiator fins which customarily consist of an Al alloy may be advantageously coated with the substance according to the invention. The shafts of air-conditioning systems in buildings may also be designed in an antimicrobial fashion by adding the active substance to the shaft material or by coating the shaft material with it. Air humidifiers may also be provided with corresponding antimicrobial properties.

Moreover, it is preferred to use the substance according to the invention in cables, in particular in cables containing polyurethane.

This represents only an example-like enumeration of possible advantageous applications. Moreover, the substance according to the invention can be used in all cases in which nanosilver is already used or people already started to think about it. Here, it must be taken into consideration that, depending upon the field of application, the requirements to be met regarding antimicrobial effectiveness, thrombogeneity and zytotoxicity are different.

The invention is further characterized by the following items:

1. A composite material made of an antimicrobially active substance containing molybdenum and/or tungsten and one or more material(s), characterized in that at least one material contains a polymer matrix which is formed from a cross-linkable polymer mixture, the cross-linkable polymer mixture containing an unsaturated polyolefin (A) which has a total amount of carbon-carbon double bonds/1000 carbon atoms of more than 0.37.
2. The composite material according to item 1, characterized in that the cross-linkable polymer mixture contains a further copolymer (B).
3. The composite material according to item 1 or 2, characterized in that the mass content of the substance is 0.1 to 50% by volume in the composite material.
4. The composite material according to any of items 1 to 3, characterized in that the surface of the substance is at least partially oxidized.
5. The composite material according to any of items 1 to 4, characterized in that the substance is molybdenum oxide or tungsten oxide.
6. The composite material according to any of items 1 to 4, characterized in that the substance is molybdenum, a molybdenum alloy and/or a molybdenum compound, the surface having an Mo oxide layer.
7. The composite material according to any of items 1 to 4, characterized in that the substance is tungsten, a tungsten alloy and/or a tungsten compound, the surface having a tungsten oxide layer.
8. The composite material according to item 6, characterized in that the molybdenum compound is Mo with from 0.1 to 1% by weight of $La_2O_3$, Mo with 0.5% by weight of Ti, 0.08% by weight of Zr, from 0.01 to 0.04% by weight of C, Mo with from 5 to 50% by weight of Re or Mo with 1.2% by weight of Hf, from 0.02 to 0.15% by weight of C.
9. The composite material according to item 6, characterized in that the molybdenum compound is molybdenum carbide, molybdenum nitride, molybdenum silicide and/or molybdenum sulfide.
10. The composite material according to item 7, characterized in that the tungsten alloy is W with from 0.1 to 1% by weight of $La_2O_3$ or W with from 1 to 26% by weight of Re.
11. The composite material according to item 7, characterized in that the tungsten compound is tungsten carbide, tungsten nitride, tungsten silicide and/or tungsten sulfide.
12. The composite material according to any of items 1 to 11, characterized in that the unsaturated polyolefin (A) of the cross-linkable polyolefin mixture is produced by means of polymerization from an olefin monomer and at least one polyunsaturated monomer.
13. The composite material according to item 12, characterized in that the olefin monomer is ethylene.
14. The composite material according to item 12, characterized in that the polyunsaturated monomer is a diene.
15. The composite material according to item 14, characterized in that the polyunsaturated component consists either of
   a) a carbon chain that is free from heteroatoms and contains at least of 8 carbon atoms and at least 4 carbon atoms between the non-conjugated double bonds, at least one of which being in a terminal position, or b) an α,ω-divinyl siloxane according to the formula I

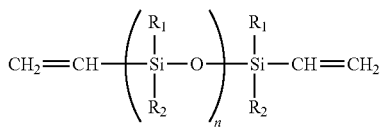

wherein R1 and R2 may be different or similar alkyl groups consisting of 1 to 4 carbon atoms and an alkoxy group, which, in turn, has 1 to 4 carbon atoms, and n=1-200.
or
c) an α,ω-divinyl ether according to the formula II

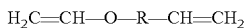

wherein R is a —$(CH_2)_m$—O—, or a —$(CH_2CH_2O)_n$— or —$CH_2$—$C_6H_{10}$—$CH_2$—O— and m=2 to 10 and n=1 to 5,
d) or a mixture of a), b) and/or c).
16. The composite material according to items 1 to 15, characterized in that the copolymer (B) is polar.
17. The composite material according to item 16, characterized in that the polar copolymer is produced by means of polymerization from one olefin and at least one polar copolymer.
18. A use of the composite material according to items 1 to 17 in articles in which microbial growth is to be avoided.
19. The use according to item 18, characterized in that the article is a medical product.
20. The use according to item 19, characterized in that the product is a port catheter comprising a chamber with a silicone membrane and a connected tube, the chamber and/or the tube consisting of the composite material according to items 1 to 17.
21. The use according to item 20, characterized in that the product is a Luer lock connection, a three-way cock and/or a cock bench.

The invention is explained in greater detail in the following by means of examples.

Table 1 contains indications on the production of samples.

Table 2 shows the effectiveness against *Staphylococcus aureus*, Table 3 that against *Escherichia coli* and Table 4 that against *Pseudomonas aeruginosa*.

EXAMPLES

The examined substances are shown in Table 1. Table 1 also contains the constitution of the starting materials and a rough description of the production of samples. The pressing process was implemented in a die press at a pressing pressure of approx. 250 MPa for the samples W 02, W 03, W 04, W 05, Mo 02, Mo 03, Mo 04 and Mo 05 according to the invention. The sintering process was implemented for these samples in a tungsten tube furnace at a temperature of 850° C. for 60 minutes under a pure hydrogen atmosphere. Unalloyed tungsten (sample W 09) and unalloyed molybdenum (sample Mo 09) were isostatically pressed at 220 MPa, sintered at a temperature of 2250° C. for 4 hours and/or of 2100° C. for 4 hours and subsequently subjected to a roll bending process, the degree of deformation being approx. 70%.

TransOptic, an acrylic resin, from the Bühler company was used as a polymer matrix for the production of the polymer matrix composite materials, which customarily is used for the production of polished sections. Atmospheric plasma spraying was used for depositing the molybdenum layers (samples SL 50, SL 51, SL 52). Here, the layer thickness was approx. 100 μm and the layer density was 85% of the theoretical density. Since the coating process was carried out on exposure to air, the oxygen content in the layer was approx. 1.5% by weight. Here, the oxygen was mainly present in the form of $MoO_3$. The molybdenum layers were deposited on a titanium alloy (SL 50), niobium (SL 51) and an intermetallic material (SL 52).

Unalloyed copper (Cu 01), unalloyed silver (SL 14), 20% by weight of copper powder, embedded in a plastic matrix (SL 20), 50% by weight of copper powder, embedded in a plastic matrix (SL 20), 20% by weight of silver, embedded in a plastic matrix (SL 21) and 50% by weight of silver, embedded in a plastic matrix (SL 27) were used as comparative samples. Moreover, the antimicrobial effectiveness of a number of further materials based on niobium, tantalum and titanium was determined for comparative purposes.

The roll-out culture already described was used for examining the antimicrobial effectiveness. The examinations were separately carried out for *Pseudomonas aeruginosa*, *Escherichia coli* and *Staphylococcus aureus*. For this purpose, the active-substance sample was added to a germ suspension. A growth of germs on the surface took place. The samples were rolled across a so-called agar plate after 3, 6, 9 and 12 hours and added to a sterile physiological saline solution. After this rolling process a photograph of the agar plate was taken and assessed as regards the germ-reducing and/or germ-killing effect. The photographs and the evaluation of the effectiveness for *Staphylococcus aureus* are shown in Table 2, those for *Escherichia coli* in Table 3 and those for *Pseudomonas aeruginosa* in Table 4.

Here, it can be seen that all substances based on tungsten or molybdenum are at least equal to pure silver in a compact form or partly clearly excel it in their antimicrobial effectiveness. Samples which, in addition to molybdenum, contain silver or copper or, in addition to tungsten, contain silver or copper proved to be especially effective.

Polymer matrix composite materials containing molybdenum oxide or tungsten oxide must also be assessed as having a good antibacterial effectiveness. The use of fine-grained powder, preferably with a particle size in accordance with Fisher of less than 5 μm, is advantageous.

With the exception of the samples mixed with Cu, samples based on tantalum or niobium do not have any effectiveness. The high antimicrobial effectiveness of copper, which, however, is accompanied by a zytotoxicity, comes to fruition in Ta—Cu and Nb—Cu.

The effectiveness of the comparative samples based on titanium must also be assessed as negative.

The tests with polymer matrix materials showed that the effectiveness can be controlled by means of the amount and the particle size of the added molybdenum and/or tungsten powder(s). The finer the molybdenum and/or tungsten powder(s) is (are), the higher is its (their) effectiveness (SL 33, SL 34). Here, molybdenum oxide powder has a greater antimicrobial effect than molybdenum metal powder (SL 22, SL 33).

Apart from the samples listed here niobium oxide, silicon carbide and manganese oxide had an antimicrobial effect which is attributable to a lowering of the pH value.

Moreover, first tests regarding zytotoxicity were also carried out. It became apparent that all copper-containing materials are zytotoxic. First tests regarding the thrombogeneity were also carried out. Silver-containing tungsten alloys have a higher thrombogeneity as compared with silver-containing molybdenum alloys. However, it must be restrictively remarked that the surface quality also influences the results.

Tests with water-soluble molybdenum and tungsten salts were also carried out to determine the mechanism of action. For this purpose, sodium molybdate ($Na_2MoO_4$) and tungsten molybdate ($Na_2WO_4$) were embedded in a plastic matrix and subjected to the test described above to determine the antimicrobial effectiveness.

Here, no lowering of the pH value of the physiological saline solution occurred. The samples were antimicrobially ineffective. Then, the content of dissolved elements in the saline solution was determined after an age-hardening time of 24 hours. As was to be expected this value was very high for the water-soluble compounds. A molybdenum content in the saline solution of 50 mg/l·cm² was e.g. determined for the sodium molybdate. By way of comparison this value is 0.1 (sample SL 18), 0.4 (sample SL 22) and 0.4 mg/l·cm² (sample SL 24) for the antimicrobially active substances. Consequently, the antimicrobial effectiveness does not correlate with the content of molybdenum or tungsten in the physiological saline solution.

Similar results were also obtained for sodium tungstate. Here, the content of tungsten in the saline solution was 324 mg/l·cm². By way of example, values of 0.1 for the sample SL 17, 0.3 for the sample SL 19 and 0.9 mg/l·cm² for the sample SL 35 were measured.

The silver content after an age-hardening of 24 hours in a physiological saline solution was determined for silver-containing materials, e.g. W 02 and W 03. Here, the values for W 02 were 28.6 and those for W 03 were 68.2 mg/l·cm².

As is known from the literature silver acts antimicrobially through the formation of $Ag^+$ ions. The effectiveness increases with increasing $Ag^+$ concentration. However, it was not possible to ascertain any dependence of the antimicrobial effectiveness on the content of molybdenum and/or tungsten in the physiological saline solution for molybdenum and tungsten. Consequently, it must be proceeded from the fact that molybdenum and tungsten per se are not active. Consequently, the pH value of the physiological saline solution was determined after the end of the test. The pH value was approximately neutral for materials that do not have any antimicrobial effect such as tantalum, tantalum-5Ag, tantalum-20Ag, niobium, niobium-5Ag, niobium-20Ag. Pure silver does also not cause any lowering of the pH value.

However, it was possible to ascertain a lowering of the pH value in all samples according to the invention. The pH value for W 09 was 4.8, for W 02 it was 3.3, for W 03 it was 3.1, for a sample of tungsten carbide with 20% by weight of silver it was 5.3, for Mo 09 it was 4.0, for Mo 02 it was 3.9 and for Mo 03 it was 3.8. The lowering of the pH value is attributable to the formation of oxonium ions ($H_3O^+$). These are formed from the reaction of $H_2MoO_4$ and/or $H_2WO_4$ with water, releasing $MoO_4^-$, $MoO_4^{2-}$ bzw. $WO_4^-$ or $WO_4^{2-}$.

$H_2MoO_4$ and/or $H_2WO_4$ are again formed from the reaction of $MoO_3$ and/or $WO_3$ with $H_2O$ and/or dissolved oxygen.

TABLE 1

Indications on the production of samples

| Material [% by weight] (designation) | Remark | Starting materials | Production of samples |
|---|---|---|---|
| Unalloyed tungsten, oxidized (W_09) | According to the invention | W powder: Fisher grain size 4.0 μm | Pressing → sintering → reshaping → mechanical processing → oxidation (dense material) |
| W—5Ag (W_02) | According to the invention | W powder: Fisher grain size 4.0 μm Ag powder: Fisher grain size 1.0 μm | Mixing → pressing → sintering → mechanical processing (porous material: 60-70% of the theoretical density) |
| W—20Ag (W_03) | According to the invention | W powder: Fisher grain size 4.0 μm Ag powder: Fisher grain size 1.0 μm | Mixing → pressing → sintering → mechanical processing (porous material: 60-70% of the theoretical density) |
| W—5Cu (W_04) | According to the invention | W powder: Fisher grain size 4.0 μm Cu powder: Fisher grain size 6.9 μm | Mixing → pressing → sintering → mechanical processing (porous material: 60-70% of the theoretical density) |
| W—20Cu (W_05) | According to the invention | W powder: Fisher grain size 4.0 μm Cu powder: Fisher grain size 6.9 μm | Mixing → pressing → sintering → mechanical processing (porous material: 60-70% of the theoretical density) |
| Plastic matrix + 20W powder (SL_17) | According to the invention | W powder: Fisher grain size 4.0 μm plastic matrix: TransOptic powder from Buehler GmbH (acrylic resin) | Mixing → pressing → mechanical processing |
| Plastic matrix + 50W powder (SL_23) | According to the invention | W powder: Fisher grain size 4.0 μm plastic matrix: TransOptic powder from Buehler GmbH (acrylic resin) | Mixing → pressing → mechanical processing |
| Plastic matrix + 20(W20Ag) powder (SL_19) | According to the invention | W powder: Fisher grain size 4.0 μm Ag powder: Fisher grain size 1.0 μm plastic matrix: TransOptic | Mixing → pressing → mechanical processing |

TABLE 1-continued

Indications on the production of samples

| Material [% by weight] (designation) | Remark | Starting materials | Production of samples |
|---|---|---|---|
| | | powder from Buehler GmbH (acrylic resin) | |
| Plastic matrix + 50(W20Ag) powder (SL_25) | According to the invention | W powder: Fisher grain size 4.0 μm Ag powder: Fisher grain size 1.0 μm Kunststoffmatrix: TransOptic powder from Buehler GmbH (acrylic resin) | Mixing → pressing → mechanical processing |
| Plastic matrix + 50WO3 powder (SL_35) | According to the invention | WO3 powder: Fisher grain size 12 μm plastic matrix: TransOptic powder from Buehler GmbH (acrylic resin) | Mixing → pressing → mechanical processing |
| Unalloyed molybdenum, oxidized (Mo_09) | According to the invention | Mo powder: Fisher grain size 3.8 μm | Pressing → sintering → reshaping → mechanical processing → oxidation (dense material) |
| Mo—5Ag (Mo_02) | According to the invention | Mo powder: Fisher grain size 3.8 μm Ag powder: Fisher grain size 1.0 μm | Mixing → pressing → sintering → mechanical processing (porous material: 60-70% of the theoretical density) |
| Mo—20Ag (Mo_03) | According to the invention | Mo powder: Fisher grain size 3.8 μm Ag powder: Fisher grain size 1.0 μm | Mixing → pressing → sintering → mechanical processing (porous material: 60-70% of the theoretical density) |
| Mo—5Cu (Mo_04) | According to the invention | Mo powder: Fisher grain size 3.8 μm Cu powder: Fisher grain size 6.9 μm | Mixing → pressing → sintering → mechanical processing (porous material: 60-70% of the theoretical density) |
| Mo—20Cu (Mo_05) | According to the invention | Mo powder: Fisher grain size 3.8 μm Cu powder: Fisher grain size 6.9 μm | Mixing → pressing → sintering → mechanical processing (porous material: 60-70% of the theoretical density) |
| Plastic matrix + 20Mo powder (SL_16) | According to the invention | Mo powder: Fisher grain size 3.8 μm plastic matrix: TransOptic powder from Buehler GmbH (acrylic resin) | Mixing → pressing → mechanical processing |
| Plastic matrix + 50Mo powder (SL_22) | According to the invention | Mo powder: Fisher grain size 3.8 μm plastic matrix: TransOptic powder from Buehler GmbH (acrylic resin) | Mixing → pressing → mechanical processing |
| Plastic matrix + 20(Mo20Ag) powder (SL_18) | According to the invention | Mo powder: Fisher grain size 3.8 μm Ag powder: Fisher grain size: 1.0 μm plastic matrix: TransOptic powder from Buehler GmbH (acrylic resin) | Mixing → Pressing → mechanical processing |
| Plastic matrix + 50(Mo20Ag) powder (SL_24) | According to the invention | Mo powder: Fisher grain size 3.8 μm Ag powder: Fisher grain size: 1.0 μm plastic matrix: TransOptic powder from Buehler GmbH (acrylic resin) | Mixing → pressing → mechanical processing |

TABLE 1-continued

Indications on the production of samples

| Material [% by weight] (designation) | Remark | Starting materials | Production of samples |
|---|---|---|---|
| Plastic matrix + 50MO$_2$ powder (SL__33) | According to the invention | MoO$_2$ powder: Fisher grain size 3.6 μm plastic matrix: TransOptic powder from Buehler GmbH (acrylic resin) | Mixing → pressing → mechanical processing |
| Plastic matrix + 50MO$_3$ powder (SL__34) | According to the invention | MoO$_3$ Pulver: Fisher grain size 15.9 μm plastic matrix: TransOptic powder from Buehler GmbH (acrylic resin) | Mixing → pressing → mechanical processing |
| Ti—46.5Al—4(Cr,Nb,Ta,B), coated with molybdenum (SL__50) | According to the invention | melting ingot | Extruding → mechanical processing → Mo coating by means of atmospheric plasma spraying |
| Unalloyed niobium, coated with molybdenum (SL__51) | According to the invention | Nb powder: Fisher grain size 4.7 μm | Pressing → sintering → reshaping → mechanical processing → Mo coating by means of atmospheric plasma spraying |
| Ti—6Al—4V—2Ag coated with molybdenum (SL__52) | According to the invention | melting ingot | Mechanical processing → Mo coating by means of atmospheric plasma spraying |
| Unalloyed tantalum (Ta__01) | Not according to the invention | Ta powder: Fisher grain size 11.0 μm | Pressing → sintering → reshaping → mechanical processing (dense material) |
| Ta—5Ag (Ta__02) | Not according to the invention | Ta powder: Fisher grain size 11.0 μm Ag powder: Fisher grain size 1.0 μm | Mixing → pressing → sintering → mechanical processing (porous material: 60-70% of the theoretical density) |
| Ta—20Ag (Ta__03) | Not according to the invention | Ta powder: Fisher grain size 11.0 μm Ag powder: Fisher grain size 1.0 μm | Mixing → pressing → sintering → mechanical processing (porous material: 60-70% of the theoretical density) |
| Ta—5Cu (Ta__04) | Not according to the invention | Ta powder: Fisher grain size 11.0 μm Cu powder: Fisher grain size 6.9 μm | Mixing → pressing → sintering → mechanical processing (porous material: 60-70% of the theoretical density) |
| Ta—20Cu (Ta__05) | Not according to the invention | Ta powder: Fisher grain size 11.0 μm Cu powder: Fisher grain size 6.9 μm | Mixing → pressing → sintering → mechanical processing (porous material: 60-70% of the theoretical density) |
| Unalloyed Niobium (Nb__01) | Not according to the invention | Nb powder: Fisher grain size 4.7 μm | Pressing → sintering → reshaping → mechanical processing (dense material) |
| Nb—5Ag (Nb__02) | Not according to the invention | Nb powder: Fisher grain size 4.7 μm Ag Pulver: Fisher grain size 1.0 μm | Mixing → pressing → sintering → mechanical processing (porous material: 60-70% of the theoretical density) |
| Nb—20Ag (Nb__03) | Not according to the invention | Nb powder: Fisher grain size 4.7 μm Ag powder: Fisher grain size 1.0 μm | Mixing → pressing → sintering → mechanical processing (porous material: 60-70% of the theoretical density) |
| Nb—5Cu (Nb__04) | Not according to the invention | Nb powder: Fisher grain size 4.7 μm Cu powder: Fisher grain size 6.9 μm | Mixing → pressing → sintering → mechanical processing (porous material: 60-70% of the theoretical density) |
| Nb—20Cu (Nb__05) | Not according to the invention | Nb powder: Fisher grain size 4.7 μm Cu powder: Fisher | Mixing → pressing → sintering → mechanical processing (porous material: |

TABLE 1-continued

Indications on the production of samples

| Material [% by weight] (designation) | Remark | Starting materials | Production of samples |
|---|---|---|---|
| | | grain size 6.9 μm | 60-70% of the theoretical density) |
| Ti—6Al—4V—2Ag (IM-Ti_01) | Not according to the invention | Melting ingot | Mechanical processing |
| Ti—46.5Al—4(Cr,Nb,Ta,B) (IM-TiAl_01) | Not according to the invention | Melting ingot | Extruding → mechanical processing |
| Unalloyed copper (Cu_01) | Prior art | Reshaped Cu rod | Mechanical processing |
| Unalloyed silver (SL_14) | Prior art | Reshaped Ag pipe | Mechanical processing |
| Plastic matrix + 20Cu powder (SL_20) | Prior art | Cu powder: Fisher grain size 6.9 μm plastic matrix: TransOptic powder from Buehler GmbH (acrylic resin) | Mixing → pressing → mechanical processing |
| Plastic matrix + 50Cu powder (SL_26) | Prior art | Cu powder: Fisher grain size 6.9 μm plastic matrix: TransOptic powder from Buehler GmbH (acrylic resin) | Mixing → pressing → mechanical processing |
| Plastic matrix + 20Ag powder (SL_21) | Prior art | Ag powder: Fisher grain size 1.0 μm plastic matrix: TransOptic powder from Buehler GmbH (acrylic resin) | Mixing → pressing → mechanical processing |
| Plastic matrix + 50Ag-powder (SL_27) | Prior art | Ag powder: Fisher grain size 1.0 μm plastic matrix: TransOptic powder from Buehler GmbH (acrylic acid) | Mixing → pressing → Mechanical processing |

TABLE 2

Effectiveness against *Staphylococcus aureus*

| Material [% by weight] (designation) | Remark | Evaluation of the effectiveness | Effectiveness after | | | | |
|---|---|---|---|---|---|---|---|
| | | | 0 h | 3 h | 6 h | 9 h | 12 h |
| Unalloyed tungsten, oxidized (W_09) | According to the invention | Satisfactory | ● | ● | ● | ● | ● |
| W—5Ag (W_02) | According to the invention | Good | ● | ● | ● | ● | ● |
| W—20Ag (W_03) | According to the invention | Very good | ● | ● | ● | ● | ● |
| W—5Cu (W_04) | According to the invention | Very good | ● | ● | ● | ● | ● |
| W—20Cu (W_05) | According to the invention | Very good | ● | ● | ● | ● | ● |
| Plastic matrix + 20W powder (SL_17) | According to the invention | Good | ● | ● | ● | ● | ● |
| Plastic matrix + 50W powder (SL_23) | According to the invention | Good | ● | ● | ● | ● | ● |
| Plastic matrix + 20(W20Ag) powder (SL_19) | According to the invention | Satisfactory | ● | ● | ● | ● | ● |
| Plastic matrix + 50(W20Ag) powder (SL_25) | According to the invention | Good | ● | ● | ● | ● | ● |
| Plastic matrix + 50WO$_3$ powder (SL_35) | According to the invention | Satisfactory | ● | ● | ● | ● | ○ |

TABLE 2-continued

Effectiveness against *Staphylococcus aureus*

| Material [% by weight] (designation) | Remark | Evaluation of the effectiveness | Effectiveness after | | | | |
|---|---|---|---|---|---|---|---|
| | | | 0 h | 3 h | 6 h | 9 h | 12 h |
| Unalloyed molybdenum, oxidized (Mo_09) | According to the invention | Good | ● | ● | ● | ● | ● |
| Mo—5Ag (Mo_02) | According to the invention | Very good | ● | ● | ● | ● | ● |
| Mo—20Ag (Mo_03) | According to the invention | Very good | ● | ● | ● | ● | ● |
| Mo—5Cu (Mo_04) | According to the invention | Very good | ● | ● | ● | ● | ● |
| Mo—20Cu (Mo_05) | According to the invention | Very good | ● | ● | ● | ● | ● |
| Plastic matrix + 20Mo powder (SL_16) | According to the invention | Good | ● | ● | ● | ● | ● |
| Plastic matrix + 50Mo powder (SL_22) | According to the invention | Good | ● | ● | ● | ● | ● |
| Plastic matrix + 20(Mo20Ag) powder (SL_18) | According to the invention | Good | ● | ● | ● | ● | ● |
| Plastic matrix + 50(Mo20Ag) powder (SL_24) | According to the invention | Good | ● | ● | ● | ● | ● |
| Plastic matrix + 50MO$_2$ powder (SL_33) | According to the invention | Good | ● | ● | ● | ● | ◯ |
| Plastic matrix + 50MO$_3$ powder (SL_34) | According to the invention | Very good | ● | ● | ● | ● | ● |
| Ti—46.5Al—4(Cr,Nb,Ta,B), coated with molybdenum (SL_50) | According to the invention | Very good | ● | ● | ● | ● | ● |
| Unalloyed niobium, coated with molybdenum (SL_51) | According to the invention | Good | ● | ● | ● | ● | ● |
| Ti—6Al—4V—2Ag, coated with molybdenum (SL_52) | According to the invention | Good | ● | ● | ● | ● | ● |
| Unalloyed tantalum (Ta_01) | Not according to invention | Poor | ● | ● | ● | ● | ● |
| Ta—5Ag (Ta_02) | Not according to invention | Poor | ● | ● | ● | ● | ● |
| Ta—20Ag (Ta_03) | Not according to invention | Poor | ● | ● | ● | ● | ● |
| Ta—5Cu (Ta_04) | Not according to invention | Very good | ● | ● | ● | ● | ● |
| Ta—20Cu (Ta_05) | Not according to invention | Very good | ● | ● | ● | ● | ● |
| Unalloyed niobium (Nb_01) | Not according to invention | Poor | ● | ● | ● | ● | ● |
| Nb—5Ag (Nb_02) | Not according to invention | Poor | ● | ● | ● | ● | ● |
| Nb—20Ag (Nb_03) | Not according to invention | Poor | ● | ● | ● | ● | ● |
| Nb—5Cu (Nb_04) | Not according to invention | Very good | ● | ● | ● | ● | ● |
| Nb—20Cu (Nb_05) | Not according to invention | Very good | ● | ● | ● | ● | ● |
| Ti—6Al—4V—2Ag (IM-Ti_01) | Not according to invention | Poor | ● | ● | ● | ● | ● |
| Ti—46.5Al—4(Cr,Nb,Ta,B) (IM-TiAl_01) | Not according to invention | Poor | ● | ● | ● | ● | ● |
| Unalloyed copper (Cu_01) | Prior art | Good | ● | ● | ● | ● | ● |
| Unalloyed silver (SL_14) | Prior art | Satisfactory | ● | ● | ● | ● | ● |
| Plastic matrix + 20Cu powder (SL_20) | Prior art | Very good | ● | ● | ● | ● | ● |
| Plastic matrix + 50Cu powder (SL_26) | Prior art | Very good | ● | ● | ● | ● | ● |
| Plastic matrix + 20Ag powder (SL_21) | Prior art | Good | ● | ● | ● | ● | ● |

TABLE 2-continued

Effectiveness against *Staphylococcus aureus*

| Material [% by weight] (designation) | Remark | Evaluation of the effectiveness | Effectiveness after | | | | |
|---|---|---|---|---|---|---|---|
| | | | 0 h | 3 h | 6 h | 9 h | 12 h |
| Plastic matrix + 50Ag powder (SL_27) | Prior art | Good | ● | ● | ● | ● | ● |

TABLE 3

Effectiveness against *Escherichia coli*

| Material [% by weight] (designation) | Remark | Evaluation of the effectiveness | Effectiveness after | | | | |
|---|---|---|---|---|---|---|---|
| | | | 0 h | 3 h | 6 h | 9 h | 12 h |
| Unalloyed tungsten, oxidized (W_09) | According to the invention | Satisfactory | ● | ● | ● | ● | ● |
| W—5Ag (W_02) | According to the invention | Very good | ● | ● | ● | ● | ● |
| W—20Ag (W_03) | According to the invention | Very good | ● | ● | ● | ● | ● |
| W—5Cu (W_04) | According to the invention | Very good | ● | ● | ● | ● | ● |
| W—20Cu (W_05) | According to the invention | Very good | ● | ● | ● | ● | ● |
| Plastic matrix + 20W powder (SL_17) | According to the invention | Not examined | Not examined | | | | |
| Plastic matrix + 50W powder (SL_23) | According to the invention | Not examined | Not examined | | | | |
| Plastic matrix + 20(W20Ag) powder (SL_19) | According to the invention | Not examined | Not examined | | | | |
| Plastic matrix + 50(W20Ag) powder (SL_25) | According to the invention | Not examined | Not examined | | | | |
| Plastic matrix + 50WO$_3$ powder (SL_35) | According to the invention | Not examined | Not examined | | | | |
| Unalloyed molybdenum, oxidized (Mo_09) | According to the invention | Satisfactory | ● | ● | ● | ● | ● |
| Mo—5Ag (Mo_02) | According to the invention | Very good | ● | ● | ● | ● | ● |
| Mo—20Ag (Mo_03) | According to the invention | Very good | ● | ● | ● | ● | ● |
| Mo—5Cu (Mo_04) | According to the invention | Very good | ● | ● | ● | ● | ● |
| Mo—20Cu (Mo_05) | According to the invention | Very good | ● | ● | ● | ● | ● |
| Plastic + 20Mo powder (SL_16) | According to the invention | Not examined | Not examined | | | | |
| Plastic matrix + 50Mo powder (SL_22) | According to the invention | Not examined | Not examined | | | | |
| Plastic matrix + 20(Mo20Ag) powder (SL_18) | According to the invention | Not examined | Not examined | | | | |
| Plastic matrix + 50(Mo20Ag) powder (SL_24) | According to the invention | Not examined | Not examined | | | | |
| Plastic matrix + 50MO$_2$ powder (SL_33) | According to the invention | Not examined | Not examined | | | | |
| Kunststoffmatrix + 50MO$_3$ powder (SL_34) | According to the invention | Not examined | Not examined | | | | |
| Ti—46.5Al—4(Cr,Nb,Ta,B) coated with molybdenum (SL_50) | According to the invention | Good | ● | ● | ● | ● | ● |
| Unalloyed niobium, coated with molybdenum (SL_51) | According to the invention | Satisfactory | ● | ● | ● | ● | ● |
| Ti—6Al—4V—2Ag, coated with molybdenum (SL_52) | According to the invention | Not examined | Not examined | | | | |
| Unalloyed tantalum (Ta_01) | Not according to invention | Poor | ● | ● | ● | ● | ● |
| Ta—5Ag (Ta_02) | Not according to invention | Poor | ● | ● | ● | ● | ● |
| Ta—20Ag (Ta_03) | Not according to invention | Poor | ● | ● | ● | ● | ● |

TABLE 3-continued

Effectiveness against *Escherichia coli*

| Material [% by weight] (designation) | Remark | Evaluation of the effectiveness | Effectiveness after | | | | |
|---|---|---|---|---|---|---|---|
| | | | 0 h | 3 h | 6 h | 9 h | 12 h |
| Ta—5Cu (Ta_04) | Not according to invention | Good | ● | ● | ● | ● | ● |
| Ta—20Cu (Ta_05) | Not according to invention | Good | ● | ● | ● | ● | ● |
| Unalloyed niobium (Nb_01) | Not according to invention | Poor | ● | ● | ● | ● | ● |
| Nb—5Ag (Nb_02) | Not according to invention | Poor | ● | ● | ● | ● | ● |
| Nb—20Ag (Nb_03) | Not according to invention | Poor | ● | ● | ● | ● | ● |
| Nb—5Cu (Nb_04) | Not according to invention | Good | ● | ● | ● | ● | ● |
| Nb—20Cu (Nb_05) | Not according to invention | Good | ● | ● | ● | ● | ● |
| Ti—6Al—4V—2Ag (IM-Ti_01) | Not according to invention | Poor | ● | ● | ● | ● | ● |
| Ti—46.5Al—4(Cr,Nb,Ta,B) (IM-TiAl_01) | Not according to invention | Poor | ● | ● | ● | ● | ● |
| Unalloyed copper (Cu_01) | Prior art | Satisfactory | ● | ● | ● | ● | ● |
| Unalloyed silver (SL_14) | Prior art | Satisfactory | ● | ● | ● | ● | ● |
| Plastic matrix + 20Cu powder (SL_20) | Prior art | Not examined | Not examined | | | | |
| Plastic matrix + 50Cu powder (SL_26) | Prior art | Not examined | Not examined | | | | |
| Plastic matrix + 20Ag powder (SL_21) | Prior art | Not examined | Not examined | | | | |
| Plastic matrix + 50Ag powder (SL_27) | Prior art | Not examined | Not examined | | | | |

TABLE 4

Effectiveness against *Pseudomonas aeruginosa*

| Material [% by weight] (designation) | Remark | Evaluation of the effectiveness | Effectiveness after | | | | |
|---|---|---|---|---|---|---|---|
| | | | 0 h | 3 h | 6 h | 9 h | 12 h |
| Unalloyed tungsten, oxidized (W_09) | According to the invention | Satisfactory | ● | ● | ● | ● | ● |
| W—5Ag (W_02) | According to the invention | Very good | ● | ● | ● | ● | ● |
| W—20Ag (W_03) | According to the invention | Very good | ● | ● | ● | ● | ● |
| W—5Cu (W_04) | According to the invention | Very good | ● | ● | ● | ● | ● |
| W—20Cu (W_05) | According to the invention | Very good | ● | ● | ● | ● | ● |
| Plastic matrix + 20W powder (SL_17) | According to the invention | Satisfactory | ● | ● | ● | ● | ● |
| Plastic matrix + 50W powder (SL_23) | According to the invention | Satisfactory | ● | ● | ● | ● | ● |
| Plastic matrix + 20(W20Ag) powder (SL_19) | According to the invention | Satisfactory | ● | ● | ● | ● | ● |
| Plastic matrix + 50(W20Ag) powder (SL_25) | According to the invention | Satisfactory | ● | ● | ● | ● | ● |
| Plastic matrix + 50WO$_3$ powder (SL_35) | According to the invention | Poor | ● | ● | ● | ● | ● |
| Unalloyed molybdenum, oxidized (Mo_09) | According to the invention | Very good | ● | ● | ● | ● | ● |

TABLE 4-continued

Effectiveness against *Pseudomonas aeruginosa*

| Material [% by weight] (designation) | Remark | Evaluation of the effectiveness | Effectiveness after 0 h | 3 h | 6 h | 9 h | 12 h |
|---|---|---|---|---|---|---|---|
| Mo—5Ag (Mo_02) | According to the invention | Very good | | | | | |
| Mo—20Ag (Mo_03) | According to the invention | Very good | | | | | |
| Mo—5Cu (Mo_04) | According to the invention | Very good | | | | | |
| Mo—20Cu (Mo_05) | According to the invention | Very good | | | | | |
| Plastic matrix + 20Mo powder (SL_16) | According to the invention | Satisfactory | | | | | |
| Plastic matrix + 50Mo powder (SL_22) | According to the invention | Satisfactory | | | | | |
| Plastic matrix + 20(Mo20Ag) powder (SL_18) | According to the invention | Satisfactory | | | | | |
| Plastic matrix + 50(Mo20Ag) powder (SL_24) | According to the invention | Satisfactory | | | | | |
| Plastic matrix + 50MO$_2$ powder (SL_33) | According to the invention | Good | | | | | |
| Plastic matrix + 50MO$_3$ powder (SL_34) | According to the invention | Very good | | | | | |
| Ti—46.5Al—4(Cr,Nb,Ta,B), coated with molybdenum (SL_50) | According to the invention | Good | | | | | |
| Unalloyed niobium, coated with molybdenum (SL_51) | According to the invention | Good | | | | | |
| Ti—6Al—4V—2Ag, coated with molybdenum (SL_52) | According to the invention | Not examined | Not examined | | | | |
| Unalloyed tantalum (Ta_01) | Not according to the invention | Poor | | | | | |
| Ta—5Ag (Ta_02) | Not according to the invention | Poor | | | | | |
| Ta—20Ag (Ta_03) | Not according to the invention | Poor | | | | | |
| Ta—5Cu (Ta_04) | Not according to the invention | Good | | | | | |
| Ta—20Cu (Ta_05) | Not according to the invention | Good | | | | | |
| Unalloyed niobium (Nb_01) | Not according to the invention | Poor | | | | | |
| Nb—5Ag (Nb_02) | Not according to the invention | Poor | | | | | |
| Nb—20Ag (Nb_03) | Not according to the invention | Poor | | | | | |
| Nb—5Cu (Nb_04) | Not according to the invention | Good | | | | | |
| Nb—20Cu (Nb_05) | Not according to the invention | Good | | | | | |
| Ti—6Al—4V—2Ag (IM-Ti_01) | Not according to the invention | Poor | | | | | |
| Ti—46.5Al—4(Cr,Nb,Ta,B) (IM-TiAl_01) | Not according to the invention | Not examined | Not examined | | | | |
| Unalloyed copper (Cu_01) | Prior art | Very good | | | | | |
| Unalloyed silver (SL_14) | Prior art | Satisfactory | | | | | |
| Plastic matrix + 20Cu powder (SL_20) | Prior art | Very good | | | | | |
| Plastic matrix + 50Cu powder (SL_26) | Prior art | Very good | | | | | |
| Plastic matrix + 20Ag powder (SL_21) | Prior art | Satisfactory | | | | | |

TABLE 4-continued

Effectiveness against *Pseudomonas aeruginosa*

| Material [% by weight] (designation) | Remark | Evaluation of the effectiveness | Effectiveness after | | | | |
|---|---|---|---|---|---|---|---|
| | | | 0 h | 3 h | 6 h | 9 h | 12 h |
| Plastic matrix + 50Ag powder (SL_27) | Prior art | Satisfactory | ● | ● | ● | ● | ● |

The invention claimed is:

1. A method for the reduction of microbial growth comprising,
forming a composite material using an inorganic substance as a component of the composite material, or using the inorganic substance as a layer or a component of a layer proximate a surface of a substrate that in combination form the composite material, the inorganic substance comprising $MoO_2$, $MoO_3$, molybdenum carbide, molybdenum nitride, molybdenum silicide, molybdenum sulfide, molybdenum hexacarbonyl, and/or molybdenum acetyl acetonate, wherein the substance is used in powder form, wherein the inorganic substance is included at a mass content of between about 3% and 50%, and wherein the substance has a particle size according to Fisher of <5 μm; and
contacting the composite material to an aqueous environment, wherein the contacting causes the formation of hydrogen cations to achieve an antimicrobial effect, and wherein, subsequent to the contacting, the aqueous environment at an interface with the composite material is characterized by a pH of less than 6.

2. The method according to claim 1, wherein the aqueous environment is water, a solution or a suspension.

3. The method according to claim 1, wherein the aqueous environment is a body fluid or liquid tissue.

4. The method according to claim 1, wherein the aqueous environment is present in the form of an adsorbed moisture film on the surface of the substance.

5. The method according to claim 1, wherein the solubility of the substance in the aqueous environment is less than 0.1 mole/liter.

6. The method according to claim 1 wherein the composite material further comprises a material which is chemically nobler than the inorganic substance.

7. The method according to claim 6, wherein the material is Ag, Cu, Sn and/or an alloy of these metals.

8. The method according to claim 1, wherein the substance is present in a dense form.

9. The method according to claim 1, wherein the substance is present in a porous form.

10. The method according to claim 1, wherein the layer is deposited by means of electron-beam evaporation, sputtering, chemical vapor deposition, electrophoresis, slurry technique, sol-gel technique or plasma spraying.

11. The method according to claim 1, wherein the layer has a spongy porous structure with a pore size of from 50 to 900 μm.

12. The method according to claim 1, wherein the substance is present in the layer in the form of island-like, substantially not linked agglomerates.

13. The method according to claim 12, wherein the average size of the individual substance agglomerates is less than 5 μm.

14. The method according to claim 12, wherein the substance agglomerates are formed by applying a slurry or by a deposition from the vapor phase and optional subsequent annealing.

15. The method according to claim 1 wherein the composite material further comprises a polymer matrix that is a highly cross-linked polyethylene.

16. The method according to claim 1 wherein the composite material comprises $Al_2O_3$—$MoO_3$, $ZrO_2$—$MoO_3$, $Al_2O_3$—Mo—$MoO_3$, $ZrO_2$—Mo—$MoO_3$, $TiO_2$—$MoO_3$, $TiO_2$—Mo—$MoO_3$, $SiO_2$—$MoO_3$, or $SiO_2$—Mo—$MoO_3$.

17. The method according to claim 16, wherein the share of $MoO_3$ is from 0.001 to 50 mole percent and the mole ratio of $ZrO_2$, $Al_2O_3$, $TiO_2$ or $SiO_2$ to $MoO_3$ is 1 to 100.

18. The method according to claim 1, wherein the substrate comprises an implant.

19. The method according to claim 18, wherein the implant is a catheter, a stent, a bone implant, a tooth implant, a vascular prosthesis or an endoprothesis.

20. The method according to claim 19, wherein the implant is a coronary stent made of nitinol, which is coated with the substance.

21. The method according to claim 19, wherein the catheter is a port catheter which comprises a chamber with a silicone membrane and a tube connected thereto, the chamber consisting of a polymer material or a material sheathed with a polymer material, which contains the substance and/or at least a part is provided with a layer containing the substance and/or the polymer material and/or the silicone membrane contains the substance.

22. The method according to claim 1, wherein the substrate comprises an absorbent sanitary article or a wound covering, wherein it contains polymer fibers or a polymer lattice, on the surface of which the substance is deposited or which contain(s) the substance.

23. The method according to claim 1, wherein the substrate comprises a filter.

24. The method according to claim 1, wherein the substrate comprises an item of clothing, which contains polymer fibers on whose surface the substance is deposited or which contain the substance.

25. The method according to claim 1, wherein the substrate comprises a layer for furnishings.

26. The method according to claim 1, wherein the substrate comprises a product which is in frequent contact with living beings.

27. The method according to claim 26, wherein the product is a switch, a fitting, a credit card, a keyboard, a cell phone housing, a coin, a bill, a door handle or part of the inside furnishings of a public means of transport.

28. The method according to claim 1, wherein the substrate comprises a container for nose sprays.

29. The method according to claim 1, wherein the substrate comprises a cable containing polyurethane.

30. The method of claim 1, wherein forming the composite material comprises:
- heating an amount of the inorganic substance and an amount of plastic material to cause cross-linking reactions of the plastic material; and
- forming a polymer matrix including the inorganic substance.

31. The method of claim 30, wherein the amount of inorganic substance is between 0.1 and 50% by volume of inorganic substance and plastic material combined.

32. The method of claim 30, wherein the polymer matrix is characterized by an elongation at break of less than 175%.

33. The method of claim 30, wherein the plastic material includes at least one item selected from the group consisting of an unsaturated polyolefin and a polar copolymer.

34. The method of claim 33, wherein the plastic material comprises an unsaturated polyolefin and a polar copolymer, wherein the polar copolymer is present from 5% to 60% by weight.

* * * * *